(12) United States Patent
Portnoy et al.

(10) Patent No.: US 9,501,619 B2
(45) Date of Patent: Nov. 22, 2016

(54) INTEGRATED MEDICATION AND INFUSION MONITORING SYSTEM

(75) Inventors: Alan M. Portnoy, Warwick, PA (US); Deborah A. Saeger, Allentown, PA (US)

(73) Assignee: Cerner Innovation, Inc., Kansas City, KS (US)

( * ) Notice: Subject to any disclaimer, the term of this patent is extended or adjusted under 35 U.S.C. 154(b) by 1997 days.

(21) Appl. No.: 12/507,113

(22) Filed: Jul. 22, 2009

(65) Prior Publication Data

US 2010/0121654 A1  May 13, 2010

Related U.S. Application Data

(60) Provisional application No. 61/114,235, filed on Nov. 13, 2008.

(51) Int. Cl.
| | |
|---|---|
| *G06Q 50/00* | (2012.01) |
| *G06Q 10/00* | (2012.01) |
| *G06F 19/00* | (2011.01) |
| *G06Q 10/10* | (2012.01) |
| *G06Q 50/24* | (2012.01) |

(52) U.S. Cl.
CPC ......... *G06F 19/325* (2013.01); *G06F 19/3468* (2013.01); *G06Q 10/1093* (2013.01); *G06Q 50/24* (2013.01)

(58) Field of Classification Search
USPC ........................................................ 705/2, 3
See application file for complete search history.

(56) References Cited

U.S. PATENT DOCUMENTS

| | | |
|---|---|---|
| 5,041,086 A | 8/1991 | Koenig et al. |
| 5,482,050 A | 1/1996 | Smokoff et al. |
| 5,590,648 A | 1/1997 | Mitchell et al. |
| 5,681,285 A | 10/1997 | Ford et al. |
| 5,772,635 A | 6/1998 | Dastur et al. |
| 5,857,194 A | 1/1999 | Keither et al. |
| 5,915,379 A | 6/1999 | Wallace et al. |
| 5,924,074 A | 7/1999 | Evans |
| 5,935,099 A | 8/1999 | Peterson et al. |

(Continued)

FOREIGN PATENT DOCUMENTS

DE   198 44 918   9/1998

*Primary Examiner* — Fonya Long
(74) *Attorney, Agent, or Firm* — Shook, Hardy & Bacon L.L.P.

(57) ABSTRACT

A System manages IV pumps so that clinicians automatically receive alerts, decisions, and actions required to maintain a patient IV medication therapy according to a prescribed treatment protocol. An infusion pump monitoring system, includes an acquisition processor for acquiring fluid infusion parameters comprising a patient identifier, infusion fluid identifier and a rate of fluid infusion, for administration of an infusion fluid to a patient at a point of care using an infusion pump. The system also includes a repository of patient medical record information. A fluid infusion monitor uses acquired fluid infusion parameters for automatically searching a patient medical record in the repository for information concerning rate of fluid infusion of a particular infusion fluid and determining if a rate of a previously administered dose of the particular infusion fluid was lower than a rate indicated in the fluid infusion parameters. An interface processor automatically initiates generation of a message indicating a potential adverse reaction to the particular infusion fluid in response to a determination of a lower rate being employed for previously administering the particular infusion fluid.

8 Claims, 9 Drawing Sheets

(56) References Cited

U.S. PATENT DOCUMENTS

| | | | |
|---|---|---|---|
| 6,095,984 | A | 8/2000 | Amano et al. |
| 6,174,283 | B1 | 1/2001 | Nevo et al. |
| 6,188,407 | B1 | 2/2001 | Smith et al. |
| 6,241,704 | B1 | 6/2001 | Peterson et al. |
| 6,269,812 | B1 | 8/2001 | Wallace et al. |
| 6,287,452 | B1 | 9/2001 | Allen et al. |
| 6,369,838 | B1 | 4/2002 | Wallace et al. |
| 6,429,869 | B1 | 8/2002 | Kamakura et al. |
| 6,475,180 | B2 | 11/2002 | Peterson et al. |
| 7,354,420 | B2 | 4/2008 | Steil et al. |
| 7,402,153 | B2 * | 7/2008 | Steil et al. .......... 604/131 |
| 2001/0031944 | A1 | 10/2001 | Peterson et al. |
| 2002/0015034 | A1 | 2/2002 | Malmborg |
| 2002/0038392 | A1 | 3/2002 | De La Huerga |
| 2002/0077852 | A1 | 6/2002 | Ford et al. |
| 2002/0077863 | A1 | 6/2002 | Rutledge et al. |
| 2002/0082867 | A1 | 6/2002 | MacCarter et al. |
| 2002/0126036 | A1 | 9/2002 | Flaherty et al. |
| 2002/0183693 | A1 | 12/2002 | Peterson et al. |
| 2002/0183976 | A1 | 12/2002 | Pearce |
| 2003/0037786 | A1 | 2/2003 | Biondi et al. |
| 2003/0092974 | A1 | 5/2003 | Santoso et al. |
| 2003/0095147 | A1 | 5/2003 | Daw |
| 2003/0236683 | A1 | 12/2003 | Henderson |
| 2004/0116804 | A1 | 6/2004 | Mostafavi |
| 2005/0126304 | A1 | 6/2005 | Goldner |
| 2007/0293843 | A1 * | 12/2007 | Ireland et al. .......... 604/504 |
| 2008/0051764 | A1 | 2/2008 | Almeda |
| 2008/0188796 | A1 | 8/2008 | Rebrin |
| 2010/0121170 | A1 * | 5/2010 | Rule .......... 600/365 |

* cited by examiner

INTEGRATED MEDICATION AND INFUSION MONITORING SYSTEM

This is a non-provisional application of provisional application Ser. No. 61/114,235 filed Nov. 13, 2008, by A. M. Portnoy et al.

FIELD OF THE INVENTION

This invention concerns an infusion pump monitoring system for monitoring rate of fluid infusion and generating alert messages based on identifying divergence of rate of administration of a dose of a particular infusion fluid to a patient on different occasions.

BACKGROUND OF THE INVENTION

A nurse and pharmacist are responsible for the care of multiple patients at any given time. This makes it difficult to monitor the status of multiple intra-venous (IV) infusion pumps and patients. This results in lapse in care of patients when infusion fluid medication bags are empty, for example. In such an event a nurse needs to call a pharmacy for a new supply of medication that results in additional delays in therapy. A system according to invention principles addresses this deficiency and related deficiencies and problems.

SUMMARY OF THE INVENTION

A system monitors infusion pumps and divergence in rate of fluid infusion on different occasions and automatically provides clinicians with data indicating alerts, a need for a treatment decisions and actions required to maintain a patient IV medication therapy to be compatible with a prescribed treatment protocol. An infusion pump monitoring system includes an acquisition processor for acquiring fluid infusion parameters comprising a patient identifier, infusion fluid identifier and a rate of fluid infusion, for administration of an infusion fluid to a patient at a point of care using an infusion pump. The system also includes a repository of patient medical record information. A fluid infusion monitor uses acquired fluid infusion parameters for automatically searching a patient medical record in the repository for information concerning rate of fluid infusion of a particular infusion fluid and determining if a rate of a previously administered dose of the particular infusion fluid was lower than a rate indicated in the fluid infusion parameters. An interface processor automatically initiates generation of a message indicating a potential adverse reaction to the particular infusion fluid in response to a determination of a lower rate being employed for previously administering the particular infusion fluid.

DETAILED DESCRIPTION OF THE INVENTION

A System manages IV pumps so that clinicians automatically receive alerts, decisions, and actions required to maintain a patient IV medication therapy according to a prescribed treatment protocol. The system automatically evaluates real-time IV activity expected for a medication protocol and a treatment plan for a patient. Further, alerts and activities are automatically initiated by the system such as to alert clinicians about an imminent decision or automatically start or stop a therapy based on pre-defined rules for therapy.

It is known that medication errors are associated with intravenous medications and infusion devices and "smart" infusion devices are used to reduce the number of errors related to medication infusion administration. Smart infusion devices provide a library of intravenous medication data with dosing parameters that reduce the risk of user programming errors. These devices are typically implemented via a wireless network that provides an easy and quick mechanism to update drug libraries and critical device information for pumps throughout a hospital facility. Smart infusion devices also provide IV bag status such that volume infused, volume remaining and infusion completion is accurately tracked and recorded. This information is received at a remote location by utilizing wireless communication that allows a nurse to optimize a nurse workflow. Smart infusion devices are also used to automate the monitoring and documentation of total fluid intake from an intravenous route (method of administration) over a period of time.

The inventors have recognized that the data provided by smart infusion devices may be advantageously processed by additionally integrating smart infusion devices with a monitoring system a Pharmacy information system and with a Barcode Point of Care system. The integrated system yields clinical, patient safety, workflow and financial benefits. A system according to invention principles utilizes data from a Smart infusion device to provide visual status indicators, via a monitoring application, to the users of a pharmacy information system or barcode point of care system (BPOC). Data is viewed at a patient level, by groups of patients or nursing units, or at a hospital wide level. The data is integrated with multiple healthcare provider applications in a Healthcare Information System (HIS) for clinical and administrative use.

Figure 1:
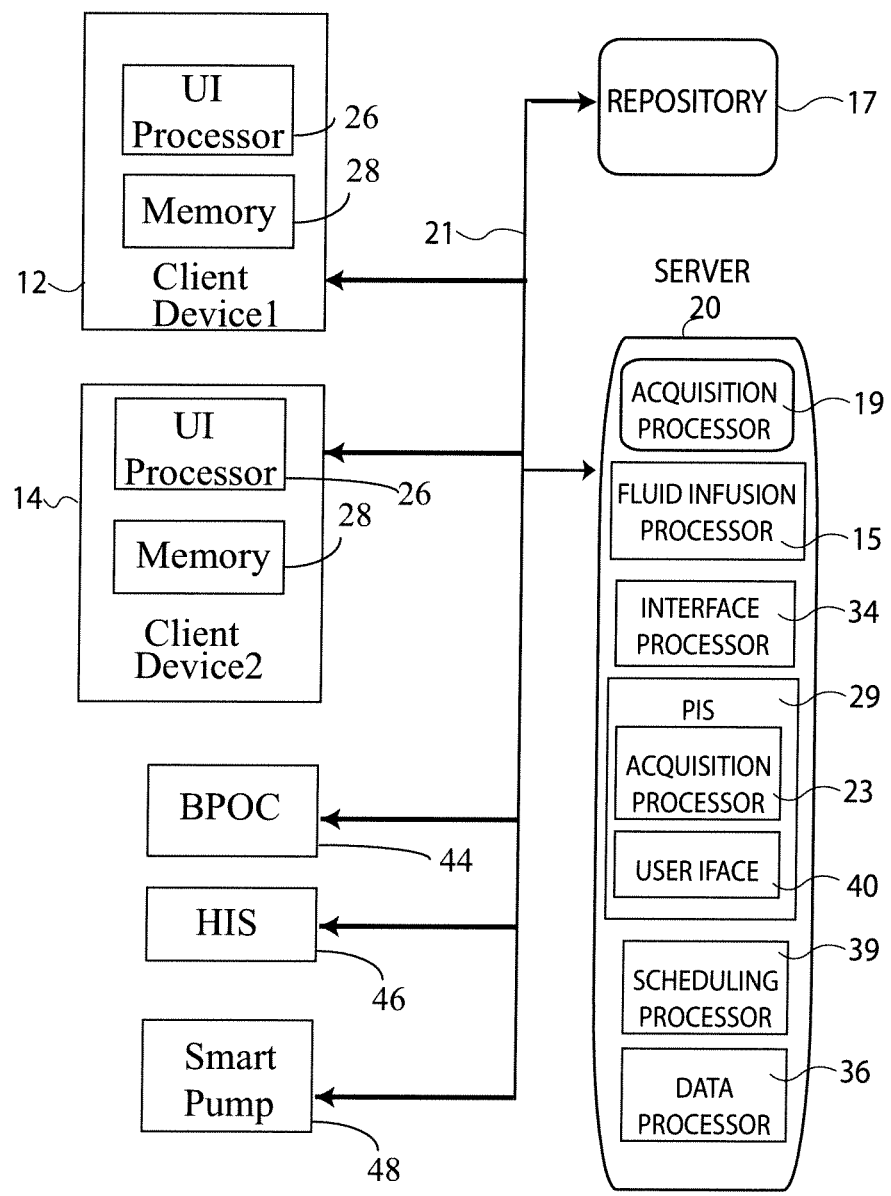
FIG. 1 shows an infusion pump monitoring system, according to invention principles.

FIG. 1 shows infusion pump monitoring system 10. System 10 includes client devices (workstations) 12 and 14, repository 17, Healthcare Information System (HIS) 46, Bar-code Point of Care (BPOC) system 44, smart pump 48 and server 20. The system 10 devices are interconnected and bidirectionally communicate via network 21 such as a LAN (Local Area Network) or other type of network. A client device (workstation) 12 or 14 includes user interface processor 26 and memory unit 28 and may comprise a personal computer, notebook, PDA or phone, for example. Repository 17 (comprising one or more local or remote databases) includes information comprising electronic patient medical record information including patient monitoring data, fluid infusion parameters including rates and other infusion related data, medical images, diagnostic related data and treatment related data. Repository 17 also includes, data representing recommended guidelines for treating different medical conditions, individual treatment order templates, medical documentation templates, treatment orders placed by physicians for patients and patient treatment plans and documentation indicating compliance with recommended treatment guidelines, for example. Server 20 comprises one or more servers or computers and includes acquisition processor 19, fluid infusion monitor (e.g., a processor) 15 interface processor 34, scheduling processor 39, data processor 36 and pharmacy information system 29. Pharmacy information system 29 includes acquisition processor 23 and user interface 40.

Acquisition processor 19 acquires fluid infusion parameters comprising a patient identifier, infusion fluid identifier and a rate of fluid infusion and at least one of, (a) a start time of infusion administration and (b) an end time of infusion administration, for administration of an infusion fluid to a patient at a point of care using an infusion pump. Fluid infusion monitor 15 uses acquired fluid infusion parameters e.g., from smart pump 48 for automatically searching a patient medical record in repository 17 for information concerning rate of fluid infusion of a particular infusion fluid and determining if a rate of a previously administered dose of the particular infusion fluid was lower than a rate indicated in the fluid infusion parameters. Interface processor 34 automatically initiates generation of a message indicating a potential adverse reaction to the particular infusion fluid in response to a determination of a lower rate being employed for previously administering the particular infusion fluid. Data processor 36 automatically predicts a time a patient receiving an administered infusion will be ready for a treatment procedure in response to the start time of infusion administration or the end time of infusion administration. Scheduling processor 39 automatically uses the time the patient will be ready for the treatment procedure in presenting a schedule identifying the treatment procedure together with a timeline.

Pharmacy information system 29 supports infusion discontinuation activity. Acquisition processor 25 acquires weaning data identifying a fluid infusion medication is being discontinued over a time period to wean a patient from the fluid infusion medication. User interface 40 automatically initiates generation of a data element for incorporation into a pharmacy information system display image for alerting a pharmacist that the fluid infusion medication is being discontinued over a time period to end at some future time and enabling a pharmacist to discontinue supplying the fluid infusion medication.

Figure 2:
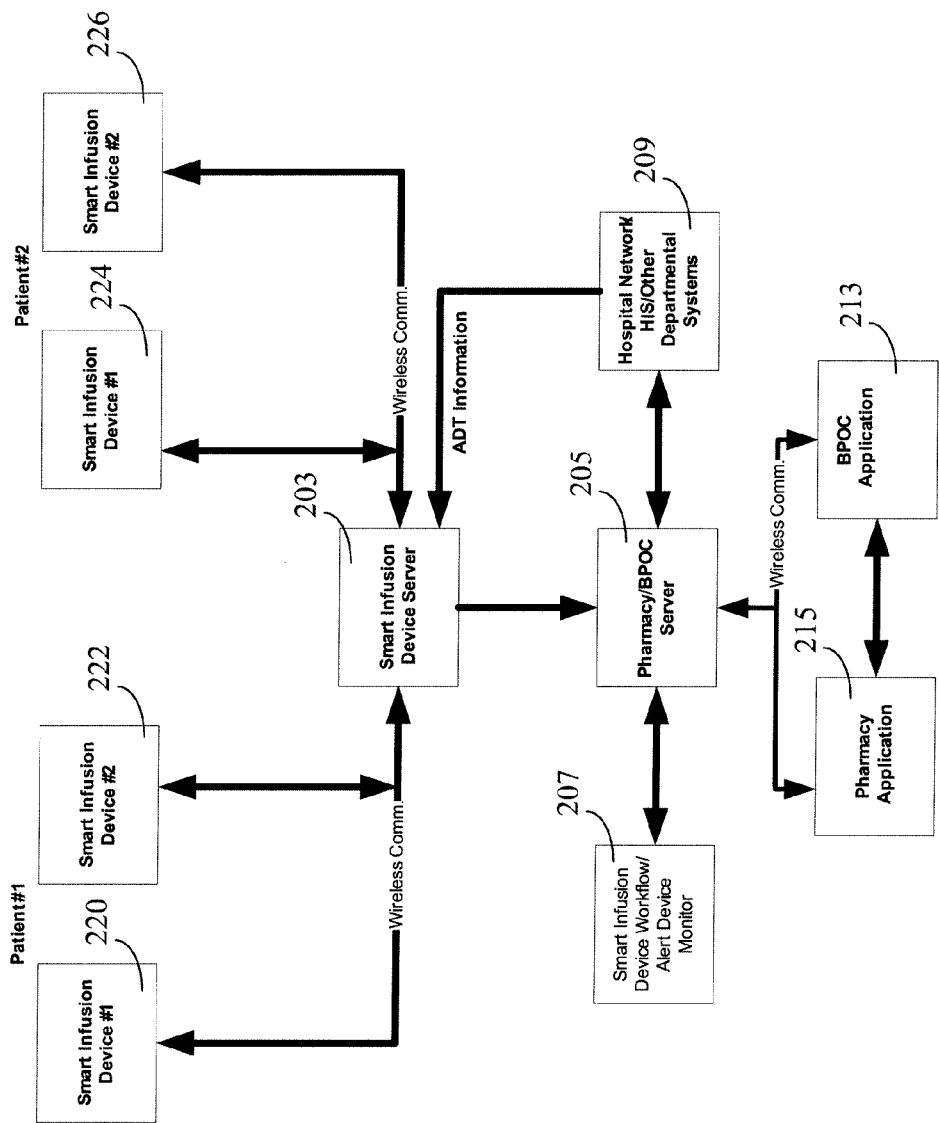
FIG. 2 shows an infusion pump monitoring system integrated with infusion pumps, a pharmacy information system and a bar-code point of care system, according to invention principles.
Figure 7:
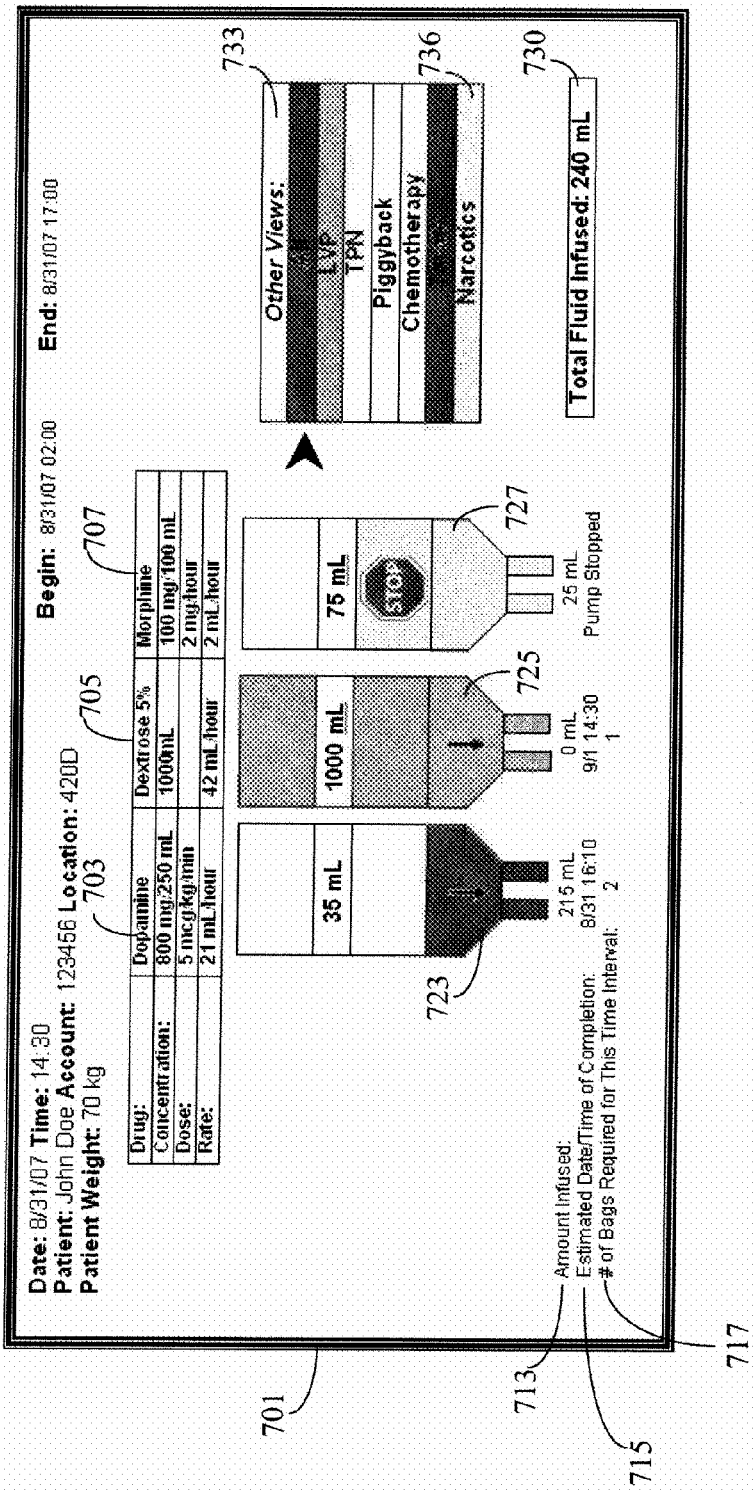
FIG. 7 shows a fluid infusion device monitor user interface display image, according to invention principles.

FIG. 2 shows infusion pump monitoring system of fluid infusion monitor 15 (FIG. 1) integrated with infusion pumps, a pharmacy information system and a bar-code point of care system. An infusion pump monitor 15 application executing on server 203 is integrated with multiple different systems including Pharmacy information system 29 (FIG. 1) and Barcode Point of Care system 44 (FIG. 1) applications 215 and 213 executing on server 205, HIS 209, infusion device workflow processor 207 and infusion pumps 220, 222, 224 and 226. Infusion pump monitor 15 bidirectionally communicates with smart infusion pump devices 220, 222, 224 and 226 via wireless or hard wired connection and thereby monitor 15 acquires IV pump information. Smart infusion pump devices 220, 222, 224 and 226 communicates information such as, but not limited to, patient identifier, pump identifier, total fluid volume in an IV bag, amount of fluid left in an IV bag, rate of IV fluid infusion, IV infusion completion time. An infusion pump monitor 15 application executing on server 203 conveys this information to the pharmacy and BPOC applications on server 205 so changes that are made directly on a pump (e.g., a fluid infusion rate change) are communicated to Pharmacy and Barcode Point of Care System applications on server 205. Infusion pump monitor 15 application on server 203 uses acquired infusion pump data to provide information on IV infusion status in a graphical format (and other formats selected via display options). Monitor 15 may be implemented in a variety of different configurations including a stand-alone application outside of Pharmacy and BPOC applications, for example. Monitor 15 provides a Graphical representation of IV bag status for a nurse and pharmacist to prioritize his or her workflow. FIG. 7 shows a fluid infusion device monitor user interface display image.

FIG. 7 shows user friendly fluid infusion device monitor display image 701 that advantageously graphically and textually presents single or combination drug infusion status of a particular patient. An alert monitor in monitor 15 directs pre-set alarms at specified IV infusion fluid volumes to initiate a workflow task sequence that alerts a pharmacist to prepare a replacement IV infusion and initiate generation of an IV bag label in the pharmacy. The alert monitor provides a nurse with an alert message via the status monitor of display image 701. This proactively alerts a nurse and pharmacist that an additional supply of medication is required for the patient before the IV bag is empty. The alert monitor is configurable to list patients and IV bag statuses by a variety of priorities such as based upon the volume of fluid left in the bag (highest to lowest, lowest to highest), listing specific critical care medications first, listing IV infusions with pump alarms first, for example. Display image 701 is configurable to display specific groups of IV infusions for a patient, such as maintenance fluids (LVP (large volume pumps), continuous infusions), IV infusion piggybacks (SVP (small volume parenteral, antibiotics), titratable IV infusions, and chemotherapy infusions).

Image 701 presents text data identifying infusion drug and associated concentration, dose and infusion rate for an infusion combination of individual drugs in columns 703, 705 and 707 respectively. Image 701 advantageously presents drug related text data in columns 703, 705 and 707 adjacent to corresponding graphical representations of infusion pump status 723, 725 and 727 depicting depletion status of the individual drugs in a view selectable via option menu 733. Menu 733 enables a user to select from views presenting all drugs being infused into a particular patient, LVP (Large Volume Pump) infused drugs, TPN (Total Parenteral Nutrition) Therapy drugs, Piggyback drugs, Chemotherapy drugs, titrated drugs and narcotic drugs. The options in menu 733 are also visually identified (e.g., by color, shading, hashing) with an attribute common to corresponding drug types graphically depicted in elements 723, 725 and 727. So for example, graphically depicted drug infusion 727 has the same color as a narcotic 736 in menu 733 identifying the drug of graphical depiction 727 as a narcotic. Further, the drug amount infused, estimated date and time of infusion completion and number of bags required is shown in rows 713, 715 and 717 adjacent to graphical representations of infusion pump status 723, 725 and 727. The graphical representation also identifies any stopped status and image 701 indicates a total infusion volume 730 of multiple drugs into a particular patient.

Figure 3:
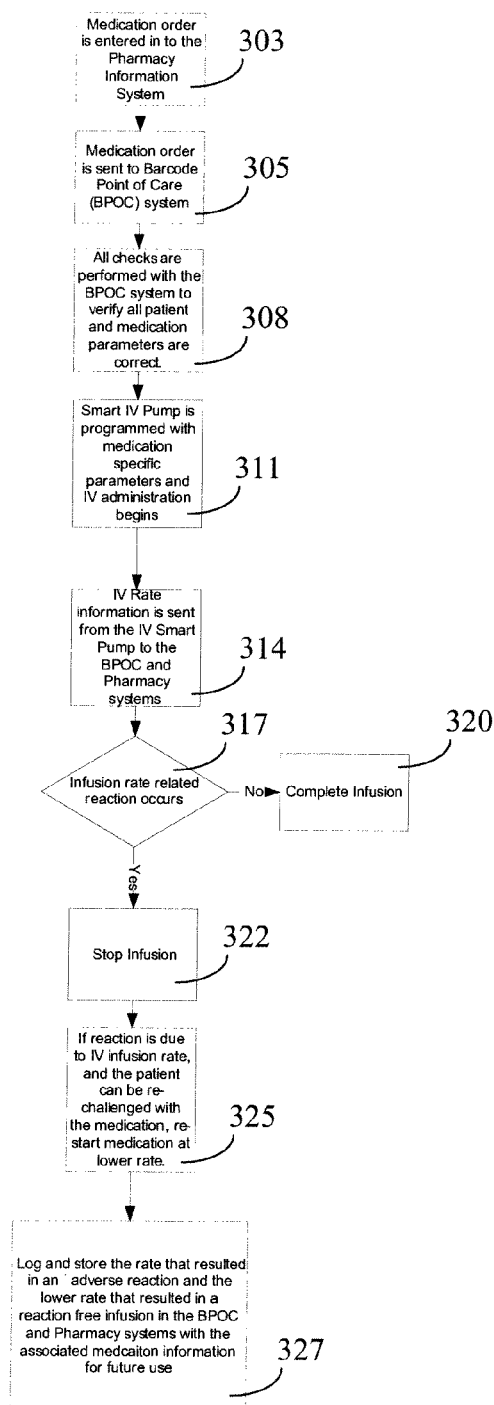
FIG. 3 shows a flowchart of a process for infusion rate monitoring and management employed on a first occasion when an infusion rate related reaction is detected by an infusion pump monitoring system, according to invention principles.

FIG. 3 shows a flowchart of a process for infusion rate monitoring and management employed on a first occasion when an infusion rate related reaction is detected by the infusion pump monitoring function of system 10 (FIG. 1). In response to a pharmacist in step 303 entering an order via client device 12 into pharmacy information system 29 for an infusion medication to be administered to a patient, an electronic medication order is sent to BPOC (bar-code point of care) system 44 in step 305. In step 308, BPOC system 44 performs safety checks, drug interaction, dosage and allergy checks using acquired data identifying both patient and medications to be administered. If a check fails, administration is terminated and an alert message is sent to a clinician for evaluation. In step 311, infusion pump monitor 15 programs infusion pump 48 with medication and patient specific infusion parameters and infusion administration is initiated. In step 314, BPOC system 44 and pharmacy information system 28 acquire data indicating rate of fluid infusion from infusion pump 48. In step 317, infusion pump monitor 15 determines from patient diagnostic and clinical documentation data or transaction messages whether the patient experiences an infusion related reaction. If no reaction is identified, infusion is completed in step 320. If a reaction is identified, infusion is terminated in step 322. In step 325 monitor 15 determines if the reaction is likely due to an excessive infusion rate and whether the infusion can be re-started, monitor 15 initiates continuation of the infusion at a lower rate determined from previous infusion rate administration data for the medication and patient concerned. In step 327, the system logs and stores data in BPOC system 44 and the pharmacy information system 29 identifying the medication and the infusion rate that resulted in the adverse reaction and the lower infusion rate that resulted in a reaction-free infusion administration.

Figure 4:
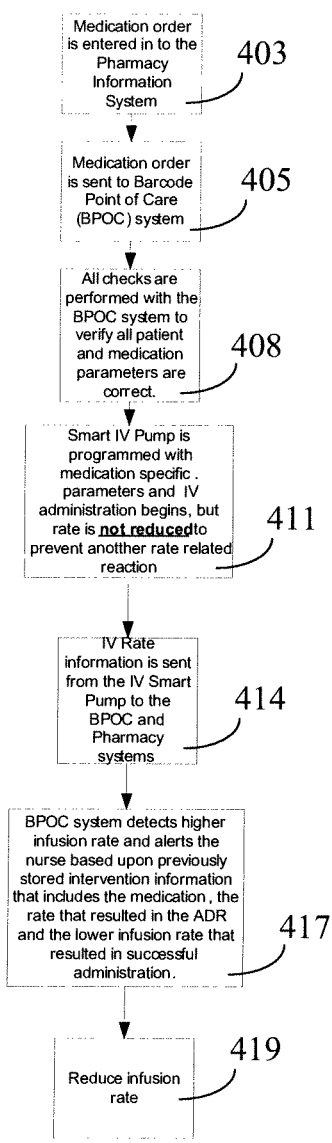
FIG. 4 shows a flowchart of a process for infusion rate monitoring and management employed on a patient subsequent visit to a healthcare provider by an infusion pump monitoring system, according to invention principles.

FIG. 4 shows a flowchart of a process performed using infusion pump monitor 15 for infusion rate monitoring and management employed on a patient subsequent visit to a healthcare provider for administration of a particular medication (following detection of an infusion rate related reaction of the particular medication in a previous visit). In response to a pharmacist in step 403 entering an order via client device 12 into pharmacy information system 29 for an infusion medication to be administered to a patient, an electronic medication order is sent to BPOC (bar-code point of care) system 44 in step 405. In step 408, BPOC system 44 performs safety checks, drug interaction, dosage and allergy checks using acquired data identifying both patient and medications to be administered. If a check fails, administration is terminated and an alert message is sent to a clinician for evaluation. In step 411, infusion pump monitor 15 programs an infusion pump with medication and patient specific infusion parameters and infusion administration is initiated. However, the infusion rate is not reduced to prevent an adverse infusion rate related reaction. In step 414, BPOC system 44 and pharmacy information system 29 acquire data indicating rate of fluid infusion from the infusion pump. In step 417, infusion pump monitor 15 determines from patient diagnostic data whether the patient experiences an infusion related reaction. If no reaction is identified, BPOC system 44 (or monitor 15 via telemetry) acquires data detecting the infusion rate and monitor 15 determines the detected rate exceeds a lower infusion rate associated with clinical data identifying a previous adverse reaction in administering an infusion of the medication. The clinical data also identifies a lower infusion rate that permitted successful infusion without an adverse reaction. Monitor 15 initiates generation of a message for communication to a nurse identifying the detected infusion rate exceeds the rate that permitted infusion without an adverse reaction. In another embodiment monitor 15 automatically initiates re-programming infusion pump 48 with the lower rate. In step 419, the infusion pump rate is reduced to the rate identified as permitting infusion without an adverse reaction and infusion continues.

Figure 5:
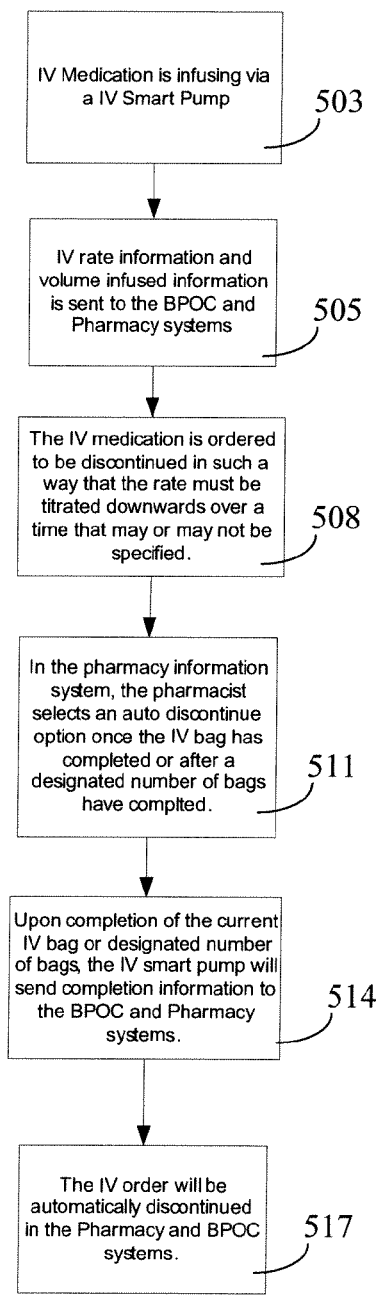
FIG. 5 shows a flowchart of a process for discontinuing an infusion medication employed by an infusion pump monitoring system, according to invention principles.

FIG. 5 shows a flowchart of a process for discontinuing an infusion medication employed by the infusion pump monitoring system of system 10 (FIG. 1). In step 503, medication is being infused into a patient via smart pump 48 (FIG. 1) and in step 505 BPOC system 44 and pharmacy information system 29 acquires data indicating rate of infusion and volume of fluid infused up to a current time from pump 48. A pharmacist in step 508 receives data indicating the medication being infused is to be discontinued in a manner in which the rate is titrated downwards over a time that may or may not be specified. The pharmacist in step 511 enters data via pharmacy information system 29 selecting an auto-discontinuation option in response to completion of the infusion or after a designated number of IV bags have been infused. In step 514, in response to completion of the infusion or after a designated number of IV bags have been infused, smart pump 48 communicates data indicating infusion completion to BPOC system 44, pharmacy system 29 or monitor 15. The infusion medication order is automatically discontinued in step 517 in the BPOC system 44 and pharmacy system 29 in response to the communicated data.

Smart infusion device 48 notifies BPOC system 44 when pre-operative antibiotics are initiated and completed. Infusion pump monitor 15 determines if a pre-defined time has passed for drug distribution to have occurred. This information is sent to an operating room system to notify workers that a patient is prepared for surgery. Monitor 15 uses the information to promptly adjust staffing schedules when a patient is inadequately medicated for a medical procedure. Administration of intravenous antibiotics needs to be initiated prior to a medical procedure so that therapy is complete and the antibiotic has been absorbed. This ensures that tissue level concentrations are adequate for surgery to begin. Improper timing and administration of intravenous antibiotics can result in post operative infections, increased morbidity and extended hospital visits. JCAHO (Joint Commission on the Accreditation of Healthcare Organizations) and CMS (Centers for Medicare & Medicaid Services) have both developed criteria for pre-operative antibiotic administration.

In an example, cardiothoracic surgery patients routinely receive a pre-operative dose of intravenous Vancomycin. This medication needs to infuse over one hour and also requires one hour for distribution to tissues. Failure to allow enough time for infusion and distribution places the patient at risk for post operative external wound infections. Some operative procedures that extend for long periods of time require an additional antibiotic dose during the procedure. BPOC system 44 and infusion monitor 15 are used in an operating room to alert a clinician to a need for additional antibiotic doses during a procedure based upon timing of administration of a pre-operative dose and the initiation of surgery. Further, monitor 15 provides a pre-set notification to pharmacy information system 29 when an IV is near completion so that a pharmacist can prepare chemotherapy medications. IV infusion fluids are often administered to patients prior to the administration of chemotherapy. A pharmacist also needs to prioritize preparation of chemotherapy medications based upon completion of administration of pre-hydration IV fluids. A notification message communicated from smart pump 48 to infusion monitor 15 prior to an IV fluid infusion completion alerts a pharmacist to begin chemotherapy preparation. Thereby a pharmacist is able prioritize workflow and reduce waste of costly chemotherapy medications.

Multiple IV medications result in infusion related adverse reactions in some patients. Allergic reactions and sudden drops in blood pressure have been associated with the infusion rate of these medications. However, there are often no other treatments that can be used as alternatives to these medications. Fortunately, many patients can tolerate these medications (such as Vancomycin, Intravenous Immune Globulin, Infliximab and Oxaliplatin) when a reduced infusion rate is used. These adverse reactions are documented using BPOC system 44 and pharmacy information system 29 in association with the medication. The documentation is stored in a patient medical record. If a medication is administered again (on a subsequent visit) at a higher infusion rate, smart pump 48 communicates IV rate information to BPOC system 44 which alerts a nurse via a display image (e.g., image 701 FIG. 7) of a prior adverse reaction and instructs the nurse to decrease the infusion rate.

Figure 6:
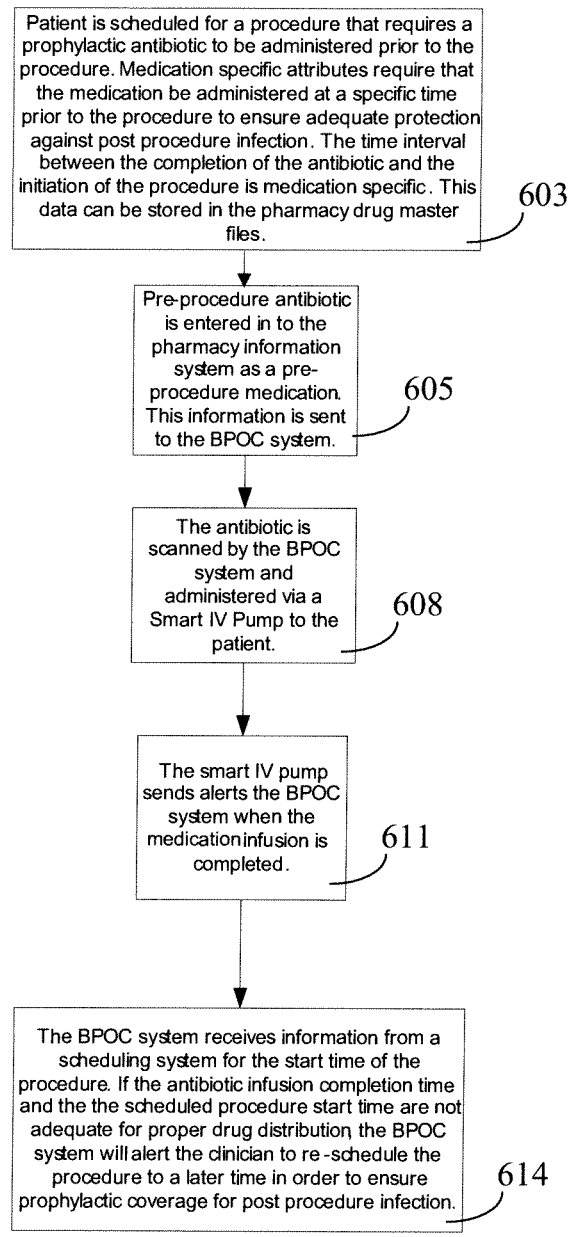
FIG. 6 shows a flowchart of a process for managing an infusion medication in conjunction with a pre-procedure medication, employed by an infusion pump monitoring system, according to invention principles.

FIG. 6 shows a flowchart of a process for managing an infusion medication in conjunction with a pre-procedure medication, employed by the infusion pump monitoring system of system 10 (FIG. 1). In step 603, a patient is scheduled for a medical procedure that requires a prophylactic antibiotic to be administered prior to the procedure. Medication specific attributes require the antibiotic to be administered at a specific time prior to the procedure to ensure adequate protection against post procedure infection. The time interval between the completion of the antibiotic and the initiation of the procedure is medication specific and stored in pharmacy drug information master files. In step 605, data indicating scheduled administration of the antibiotic is entered into pharmacy information system 29 identifying it as a pre-procedure medication and the data is also communicated to BPOC system 44 and monitor 15. In step 608 the antibiotic is scanned using BPOC system 44 and administered to a patient via smart pump 48. Smart pump 48 in step 611 sends an alert message to BPOC system 44 and monitor 15 in response to completion of the antibiotic administration. BPOC system 44 and monitor 15 receive data identifying the start time of a medical procedure associated with the antibiotic in step 614 from scheduling processor 39. BPOC system 44 and monitor 15 automatically determine from the time of completion of the antibiotic and the scheduled start time of the procedure, whether or not there is sufficient time for proper distribution of the antibiotic in the patient anatomy. If there is insufficient time, monitor 15 alerts a clinician to reschedule the procedure to a later time in order to ensure prophylactic coverage for post procedure infection. Monitor 15 also sends data to a hospital material management and inventory system in real-time to provide a snap-shot overview of the amount IV fluids being used in the hospital at any given time. Thereby supply chain ordering is dynamically adjusted reducing cost and need to maintain too much inventory.

Monitor 15 communicates an alert message to a nurse when it is time to draw a blood sample for drug levels based upon infusion time and distribution characteristics of a medication. In exemplary operation, a gentamicin IV dose may infuse over 30 minutes and take an additional 30 minutes to distribute in patient anatomy to produce an accurate peak plasma level. Upon completion of IV fluid infusion, completion indication data received from smart pump 48 is used by monitor 15 to initiate generation of an alert message for communication to notify a nurse that it is time to draw a blood sample for a peak drug level. In response to acquisition of the blood sample, a blood tube is scanned in to BPOC system 44 and monitor 15 to document time the blood sample is acquired. This information is sent to a laboratory test system along with the infusion time data to validate the accuracy of the sample. In a further example, involving Heparin protocols, protocol adjustments to IV infusion rates are based upon laboratory test results for partial thromboplastin time (aPTT) measuring the anticoagulant effect of prolongation. Smart pump 48 sends infusion rate information to infusion monitor 15 and BPOC system 44. Also aPTT test information received by Pharmacy information system 29 and BPOC system 44 and monitor 15 is compared with a current IV rate and monitor 15 generates an alert message to a clinician identifying required correct protocol adjustments. Alternatively, monitor 15 alerts a nurse if the IV rate is incorrect according to protocol.

Reimbursement regulations for continuous IV infusions require documentation of an IV infusion greater than 15 minutes in length. System 10 enables a healthcare provider to document additional reimbursement using a claim and billing processing system for outpatients receiving IV infusions as an automatic transaction directed by monitor 15. In one embodiment, an IV infusion is scanned with BPOC system 44 when an IV is started. Monitor 15 initiates calculation of duration of an infusion in response to notification from smart pump 48 indicating completion of an IV infusion. This information is stored in association with an electronic order for administration of the infusion in pharmacy information system 29 and is used for financial claim preparation. In addition, system 10 automatically discontinues an order for an infusion in Pharmacy Information System 29 in response to receiving a message identifying IV infusion completion from smart pump 48. The automatic discontinuation function is selectable by a pharmacist using Pharmacy Information System 29.

Automatic discontinuation of an IV infusion order using Pharmacy system 29 improves patient safety. System 10 enables a period of time over which medications are discontinued to be undefined. System 10 is also able to use a patient specific time duration (minutes to hours) involving slowly titrating an infusion rate downwards, until a specific patient response occurs, for example. In response to communication of information indicating an IV infusion is stopped to pharmacy information system 29, a pharmacist is able to discontinue an order for the infusion via Pharmacy system 29. However, communication between a nurse and pharmacist does not always occur as quickly as is needed, increasing a risk that a patient receives additional supplies of a medication that have been discontinued. System 10 advantageously automatically discontinues a medication by signaling to Pharmacy information system 29 that an IV infusion is completed and reduces waste of preparation of a discontinued IV infusion. Further, monitor 15 tracks where a pump is located and sends an alert message to maintenance workers when a pump fails or requires maintenance.

Nurses and other clinicians employ system 10 to monitor, respond to, and act on, real-time information that affects IV medication therapies. The information provided by infusion monitor 15 informs other clinical and administrative users of relevant treatment and administrative procedures. Infusion monitor 15 may be implemented as a stand alone system and used in areas that do not routinely have BPOC and pharmacy systems, but that have use for the data provided by monitor 15. System 10 processes data provided by smart pump 48 for integration with Pharmacy Information System 29 and BPOC System 44 using an easy to read graphical format. Data received from smart pump 48 is also used by Pharmacy and BPOC systems 29 and 44 to provide workflow and clinical and patient safety information. A Rules Engine within monitor 15 enhances the value of acquired and derived data by providing additional alert statuses based upon specific clinical conditions. Information provided by monitor 15 is communicated to other clinical and administrative systems.

Figure 8:
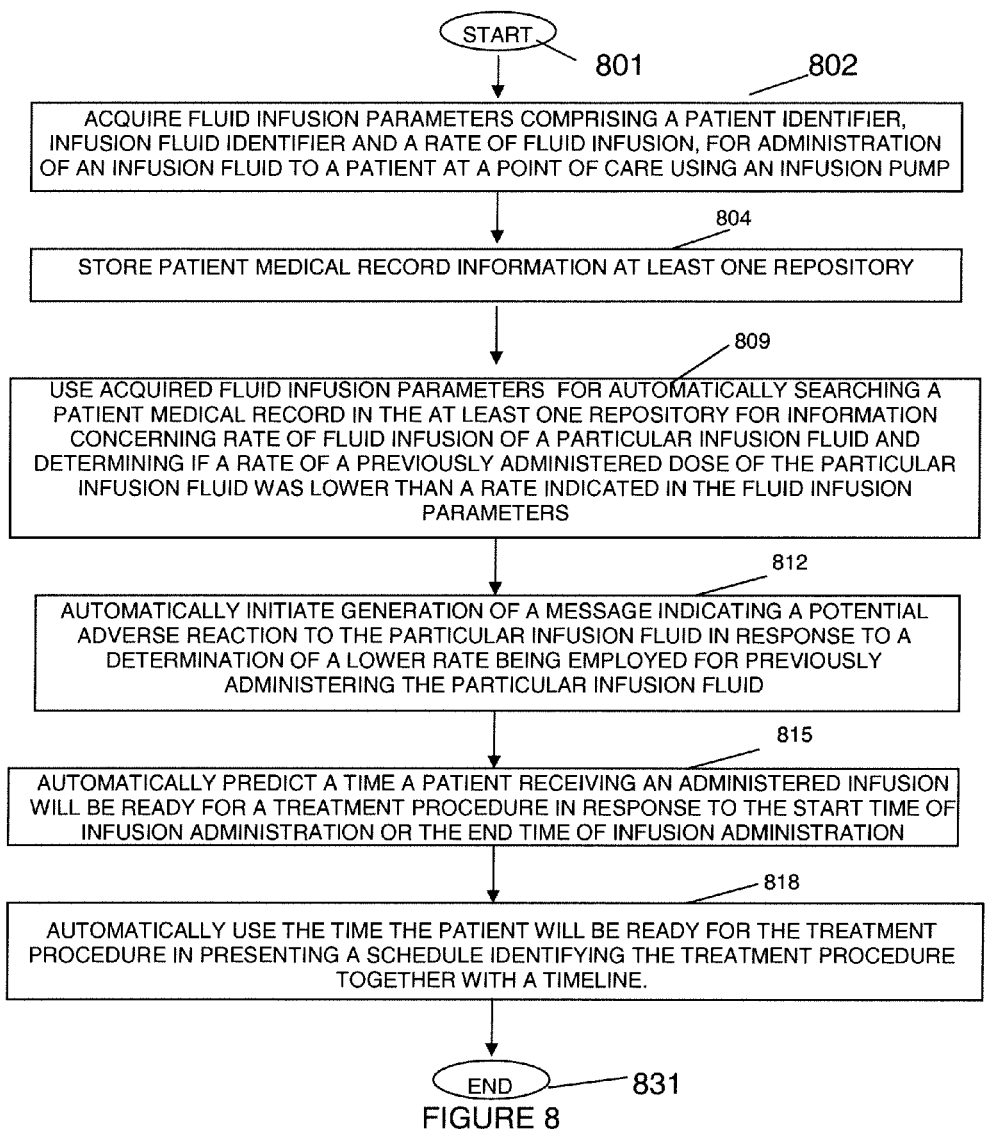
FIG. 8 shows a flowchart of a process used by an infusion pump monitoring system, according to invention principles.

FIG. 8 shows a flowchart of a process used by an infusion pump monitor 15 (FIG. 1) in system 10. In step 802 following the start at step 801, acquisition processor 19 acquires fluid infusion parameters comprising a patient identifier, infusion fluid identifier, a rate of fluid infusion and at least one of, (a) a start time of infusion administration and (b) an end time of infusion administration, for administration of an infusion fluid to a patient at a point of care using infusion pump 48. Acquisition processor 19 acquires the fluid infusion parameters from Bar-code Point of Care system 44, infusion pump 48 and HIS 46. In step 804, patient medical record information is stored in at least one repository 17. Fluid infusion monitor 15 in step 809 uses acquired fluid infusion parameters for automatically searching a patient medical record in at least one repository 17 for information concerning rate of fluid infusion of a particular infusion fluid and determining if a rate of a previously administered dose of the particular infusion fluid was lower than a rate indicated in the fluid infusion parameters.

In step 812 interface processor 34 automatically initiates generation of a message indicating a potential adverse reaction to the particular infusion fluid in response to a determination of a lower rate being employed for previously administering the particular infusion fluid for communication to pharmacy information system 29. The message comprises a displayed alert message to a healthcare worker, an indication of the lower rate employed for previously administering the particular infusion fluid or prompts a healthcare worker to lower the rate indicated in the fluid infusion parameters. Interface processor 34 also automatically initiates generation of a message for communication to infusion pump 48 to at least one of, (a) reduce rate of fluid infusion and (b) inhibit operation of infusion pump 48 until a healthcare worker enters a command to acknowledge the message indicating the potential adverse reaction in response the determination. Data processor 36 automatically predicts a time a patient receiving an administered infusion will be ready for a treatment procedure in response to the start time of infusion administration or the end time of infusion administration. Data processor 36 predicts the time the patient will be ready for the treatment procedure in response to patient demographic information including at least one of, (a) age, (b) weight and (c) gender. Scheduling processor 39 automatically uses the time the patient will be ready for the treatment procedure in presenting a schedule identifying the treatment procedure together with a timeline. The process of FIG. 8 terminates at step 831.

Figure 9:
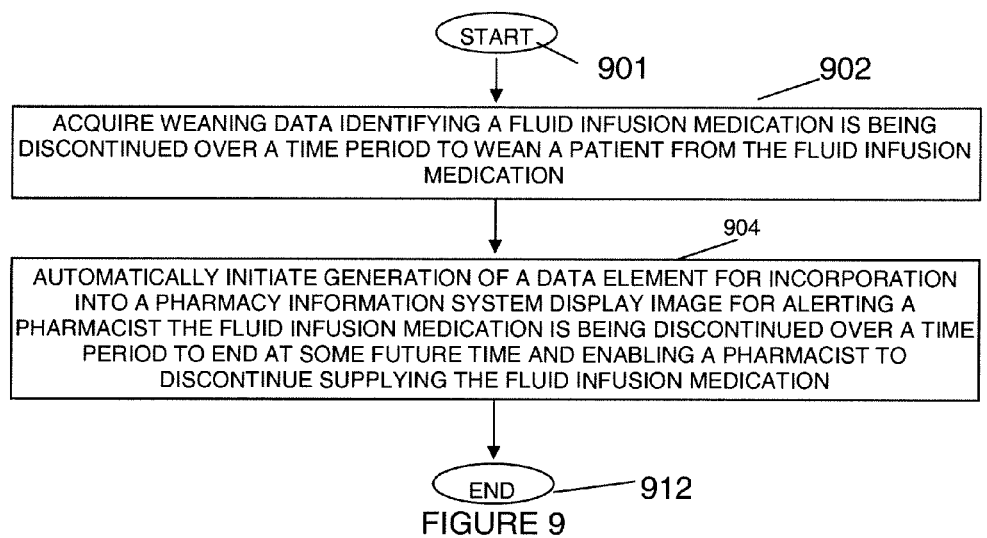
FIG. 9 shows a flowchart of a process used by a pharmacy information system supporting infusion discontinuation activity, according to invention principles.

FIG. 9 shows a flowchart of a process used by pharmacy information system 29 supporting infusion discontinuation activity. In step 902 following the start at step 901, acquisition processor 23 acquires weaning data identifying a fluid infusion medication is being discontinued over a time period to wean a patient from the fluid infusion medication. Acquisition processor 23 acquires the weaning data from Bar-code Point of Care system 44, HIS 46, pharmacy information system 29 or infusion pump 48. In step 904, user interface 40 automatically initiates generation of a data element for incorporation into a pharmacy information system 29 display image for alerting a pharmacist the fluid infusion medication is being discontinued over a time period to end at some future time and enabling a pharmacist to discontinue supplying the fluid infusion medication. The process of FIG. 9 terminates at step 912.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A document or record comprises a compilation of data in electronic form and is the equivalent of a paper document and may comprise a single, self-contained unit of information. A document or record comprises a compilation of data in electronic form and is the equivalent of a paper document and may comprise a single, self-contained unit of information.

A workflow processor in monitor 15, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams.

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The infusion pump monitoring system advantageously integrates an IV infusion pump and BPOC and pharmacy information systems. Further, the processes and applications may, in alternative embodiments, be located on one or more (e.g., distributed) processing devices on the network of FIG. 1. Any of the functions and steps provided in FIGS. 1-9 may be implemented in hardware, software or a combination of both.

What is claimed is:

1. An infusion pump monitoring system, comprising:
    an acquisition processor for acquiring fluid infusion parameters comprising a patient identifier, infusion fluid identifier and a rate of fluid infusion to be used for a patient, for administration of an infusion fluid to a patient at a point of care using an infusion pump;
    a repository of patient medical record information;
    a fluid infusion monitor for using acquired fluid infusion parameters for automatically searching a patient medical record in said repository for information concerning rate of fluid infusion of a particular infusion fluid and determining if a rate of a previously administered dose of said particular infusion fluid was lower than a rate indicated in said fluid infusion parameters; and
    an interface processor for automatically initiating generation of a message indicating a potential adverse reaction to said particular infusion fluid in response to a determination of a lower rate being employed for previously administering said particular infusion fluid to said patient, wherein said interface processor initiates generation of a message for communication to an infusion pump to at least one of, (a) reduce rate of fluid infusion and (b) inhibit operation of an infusion pump until a healthcare worker enters a command to acknowledge said message indicating said potential adverse reaction in response to said determination.

2. A system according to claim 1, wherein said medical record identifies the fluid infusion medication and the infusion rate that resulted in the adverse reaction and the lower infusion rate that resulted in a reaction-free infusion administration and said message prompts a healthcare worker to lower said rate indicated in said fluid infusion parameters.

3. A system according to claim 1, wherein said message indicating a potential adverse reaction to said particular infusion fluid comprises a displayed alert message to a healthcare worker.

4. A system according to claim 1, wherein said message indicating a potential adverse reaction to said particular infusion fluid comprises an indication of said lower rate employed for previously administering said particular infusion fluid.

5. A system according to claim 1, wherein said acquisition processor acquires said fluid infusion parameters from a Bar-code Point of Care system.

6. A system according to claim 1, wherein said acquisition processor acquires said fluid infusion parameters from an infusion pump.

7. A system according to claim 1, wherein said interface processor automatically initiates generation of a message indicating a potential adverse reaction to said particular infusion fluid for communication to a pharmacy information system.

8. A method of monitoring a plurality of medical infusion pumps, comprising the steps of:
    acquiring fluid infusion parameters comprising a patient identifier, infusion fluid identifier and a rate of fluid infusion to be used for a patient, for administration of an infusion fluid to a patient at a point of care using an infusion pump;
    storing in at least one repository, patient medical record information;
    using acquired fluid infusion parameters for automatically searching a patient medical record in said repository for information concerning rate of fluid infusion of a particular infusion fluid and determining if a rate of a previously administered dose of said particular infusion fluid was lower than a rate indicated in said fluid infusion parameters;
    automatically initiating generation of a message indicating a potential adverse reaction to said particular infusion fluid in response to a determination of a lower rate being employed for previously administering said particular infusion to said patient; and automatically initiating generation of a message for communication to an infusion pump to at least one of, (a) reduce rate of fluid infusion and (b) inhibit operation of an infusion pump until a healthcare worker enters a command to acknowledge said message indicating said potential adverse reaction in response to said determination.

* * * * *